United States Patent
Sandberg et al.

(10) Patent No.: US 6,558,543 B1
(45) Date of Patent: May 6, 2003

(54) APPARATUS FOR USE IN CONNECTION WITH REMOVAL OF ELEMENTS, ESPECIALLY EXOGENOUS ANTIBODIES, FROM BLOOD OR PLASMA

(75) Inventors: Bengt E. B. Sandberg, Hjärup (SE); Rune Nilsson, Lund (SE)

(73) Assignee: Mitra Medical Technology AB, Lund (SE)

( * ) Notice: Subject to any disclaimer, the term of this patent is extended or adjusted under 35 U.S.C. 154(b) by 0 days.

(21) Appl. No.: 09/600,446
(22) PCT Filed: Jan. 14, 1999
(86) PCT No.: PCT/IB99/00041
§ 371 (c)(1), (2), (4) Date: Aug. 9, 2000
(87) PCT Pub. No.: WO99/36110
PCT Pub. Date: Jul. 22, 1999

(30) Foreign Application Priority Data

Jan. 20, 1998 (DK) ......................................... 1998 00070

(51) Int. Cl.⁷ ........................... B01D 24/16; B01D 24/48
(52) U.S. Cl. ........................ 210/266; 210/288; 210/420
(58) Field of Search ................................ 210/266, 282, 210/288, 420

(56) References Cited

U.S. PATENT DOCUMENTS

| | | | | |
|---|---|---|---|---|
| 3,822,018 A | * | 7/1974 | Krongos | 210/420 |
| 4,498,990 A | * | 2/1985 | Shaldon et al. | 210/637 |
| 5,017,293 A | | 5/1991 | Radovich | 210/646 |

FOREIGN PATENT DOCUMENTS

| | | |
|---|---|---|
| DE | 19537688 | 5/1996 |
| EP | 0076421 | 4/1983 |
| FR | 274456 | 4/1998 |
| WO | 9212730 | 8/1992 |

* cited by examiner

Primary Examiner—Ivars Cintins
(74) Attorney, Agent, or Firm—Ladas & Parry

(57) ABSTRACT

An apparatus for use in connection with removal of elements, especially exogenous antibodies, from blood or plasma flowing in an extracorporeal blood circulation system of a patient, where said apparatus comprises a container (1). This container is adapted to receive an adsorbent and comprises an inlet (15) and an outlet (16) which are adapted to be connected to an inlet conduit (19) and an outlet conduit (20), respectively, forming part of the blood circulation system. The container (1) comprises an inlet chamber (31), an adsorption chamber (32) adapted to receive the adsorbent, and an outlet chamber (33). These chambers are arranged in sequence when seen in the flow direction of the blood or the plasma through the container (1) and are separated by means of filter units (11, 12) allowing passage of the blood or the plasma. The inlet (15) and the outlet (16) are arranged adjacent one another in connection with a common movable valve means (21). The valve means is adapted so as in a first position to connect the inlet (15) and the outlet (16) directly with their respective passages (28, 29) in the container wall (4) and so as in a second position to connect said inlet (15) and said outlet (16) with their respective ends of a bypass-forming channel (34) in the container wall (4). The passage (28) associated with the inlet communicates with a transfer channel (30) ending in the inlet chamber (31), whereas the passage (29) associated with the outlet (16) is open into the outlet chamber (33).

9 Claims, 2 Drawing Sheets

APPARATUS FOR USE IN CONNECTION WITH REMOVAL OF ELEMENTS, ESPECIALLY EXOGENOUS ANTIBODIES, FROM BLOOD OR PLASMA

TECHNICAL FIELD

The invention relates to an apparatus for use in connection with removal of elements, especially exogenous antibodies, from blood or plasma flowing in an extracorporeal blood circulation system of a patient, where said apparatus comprises a container adapted to receive an adsorbent, and where said container is provided with an inlet and an outlet adapted to be connected to an inlet conduit and an outlet conduit, respectively, forming pat of the blood circulation system.

BACKGROUND ART

It is known inter alia from WO 92/12730 to treat cancer by way of injecting antibodies containing a cytocide into the blood circulation system of a patient. From the same publication it is also known to limit the side effect of these antibodies by removing them again after a suitable period of time. In order to ensure a good result of the use of antibodies, said antibodies are administered in relatively large amounts. However, only a very small portion of the antibodies, ordinarily less than 1%, reach the cancer cells. When the remaining portion of the antibodies stay for a long period of time in the patient, said portion may involve a risk of having an injurious, damaging effect, such as when the antibodies for instance contain radioactive material.

It is also known to use a so-called column housing for removing the antibodies by way of adsorption. A suitable adsorbent is placed inside the column housing, said adsorbent ensuring the necessary effect during the passage of the blood. In the known systems the blood is directed through a pump and a device for separating the plasma to the column housing, whereby the blood cells are directed round the column housing and returned to the plasma after said plasma has passed the column housing. The column housing comprises a container with an inlet and an outlet in their respective ends. The inlet is connected to an inlet conduit and the outlet to an outlet conduit, and a shut-off valve is arranged in each of these conduits. A bypass conduit extends round the container, and one end of said bypass conduit is connected to the inlet conduit before the shut-off valve when seen in the flowing direction of the plasma, and the other end of said bypass conduit is connected to the outlet conduit after the shut-off valve therein. The bypass conduit comprises per se at least one shut-off valve. When this column housing is used, the flow through the bypass conduit is allowed by a closing of the shut-off valves in the inlet conduit and the outlet conduit in various situations, such as in connection with removal of air from the conduit system, in connection with a clogging up of the passageway through the column housing caused by for instance coagulation, and in connection with the termination of the treatment whereby a saline solution is used for expelling the plasma from the conduit system.

Such a conduit system with a column housing and a bypass conduit extending round said column housing is relatively complicated and difficult to handle. In addition, it is not suited for treatment of ordinary blood, but only of blood plasma because a high risk exists of the blood coagulating in the bypass conduit while the flow therethrough is interrupted.

BRIEF DESCRIPTION OF THE INVENTION

The object of the invention is to provide an apparatus which presents a relatively simple structure, which is easy to operate and suited for treatment of ordinary blood.

The apparatus according to the invention is characterised in that the container comprises an inlet chamber, an adsorption chamber for receiving the adsorbent, and an outlet chamber, whereby the chambers are arranged in sequence when seen in the flow direction of the blood through the container and are separated by means of filter units allowing a passage of the blood, that the inlet and the outlet are arranged adjacent one another on the portion of the container wall which together with a filter unit defines the outlet chamber and which is associated with a common movable valve means, where said valve means is adapted in a first position to connect the inlet and the outlet directly with their respective passages in the container wall, and where said valve means is adapted in a second position to connect the inlet and the outlet with their respective ends of a bypass-forming channel in the container wall, and that the passage associated with the inlet communicates with a transfer channel ending in the inlet chamber whereas the passage associated with the outlet is open into the outlet chamber.

As a result, it is sufficient to operate only one valve means, and in addition the bypass channel is relatively short. The relatively short bypass channel involves a risk of coagulation of only a very small portion of blood, said portion, if any, being easily absorbed by the patient. The apparatus in question can, of course, also be used for treatment of blood plasma. By the conventional use of the apparatus, the blood flows through the passage at the inlet of the container and then through the transfer channel to the inlet chamber, and subsequently the blood passes the filter unit therein and flows through the adsorption chamber containing the suitable adsorbent. From here the blood passes the second filter unit and enters the outlet chamber, whereafter it leaves said outlet chamber through the passage and flows to the outlet and is returned to the patient in a conventionally known manner. When it is desired to open the bypass circulation system, the valve means is activated so as to interrupt the flow through the adsorbent and open the bypass channel.

According to the invention the valve means may be permanently connected to an inlet stub and an outlet stub with the result that said stubs are easily moved together. The valve means may particularly advantageously be rotatable.

Moreover, the inlet and the outlet may according to the invention be associated with a cover accommodated on the container, said cover comprising an inner cover member in sealing connection with the opening of the container as well as an outer cover member which is secured to the container and comprises an opening surrounding the valve means, where said valve means comprises an at least partially circumferential, radially projecting flange which is received in a corresponding recess between the two cover members, stopping means being provided for stopping the rotation of the valve means at the two functional positions. The resulting embodiment is particularly simple to manufacture and operate.

In addition, the container may according to the invention be substantially axially symmetrically structured, the passage of the inlet and the associated transfer channel being arranged coaxially with the axis of symmetry of the container. In this manner an embodiment is ensured which is easy both to sterilize, to fill with adsorbent, to empty of air prior to the use as well as easy to manufacture.

According to the invention the filter units may in a particular simple manner be disc-shaped and provided with a porous filter cloth embedded in a carrying plastic structure.

Each filter unit may according to the invention particularly advantageously be retained in a sealing abutment against an associated circumferential abutment face on the inner wall of the container, said filter unit at the inlet chamber being retained by a separately secured bottom member and said filter unit at the outlet chamber being retained by the inner cover member.

Finally the transfer channel may according to the invention be formed by a tube permanently connected to the inner cover member, said tube comprising outer circumferential grooves co-operating by way of a snapping effect with a central annular member of the carrying structure of each filter unit.

BRIEF DESCRIPTION OF THE DRAWINGS

The invention is explained in greater detail below with reference to the accompanying drawing, in which.

BEST MODE OF CARRYING OUT THE INVENTION

Figures 1, 3:
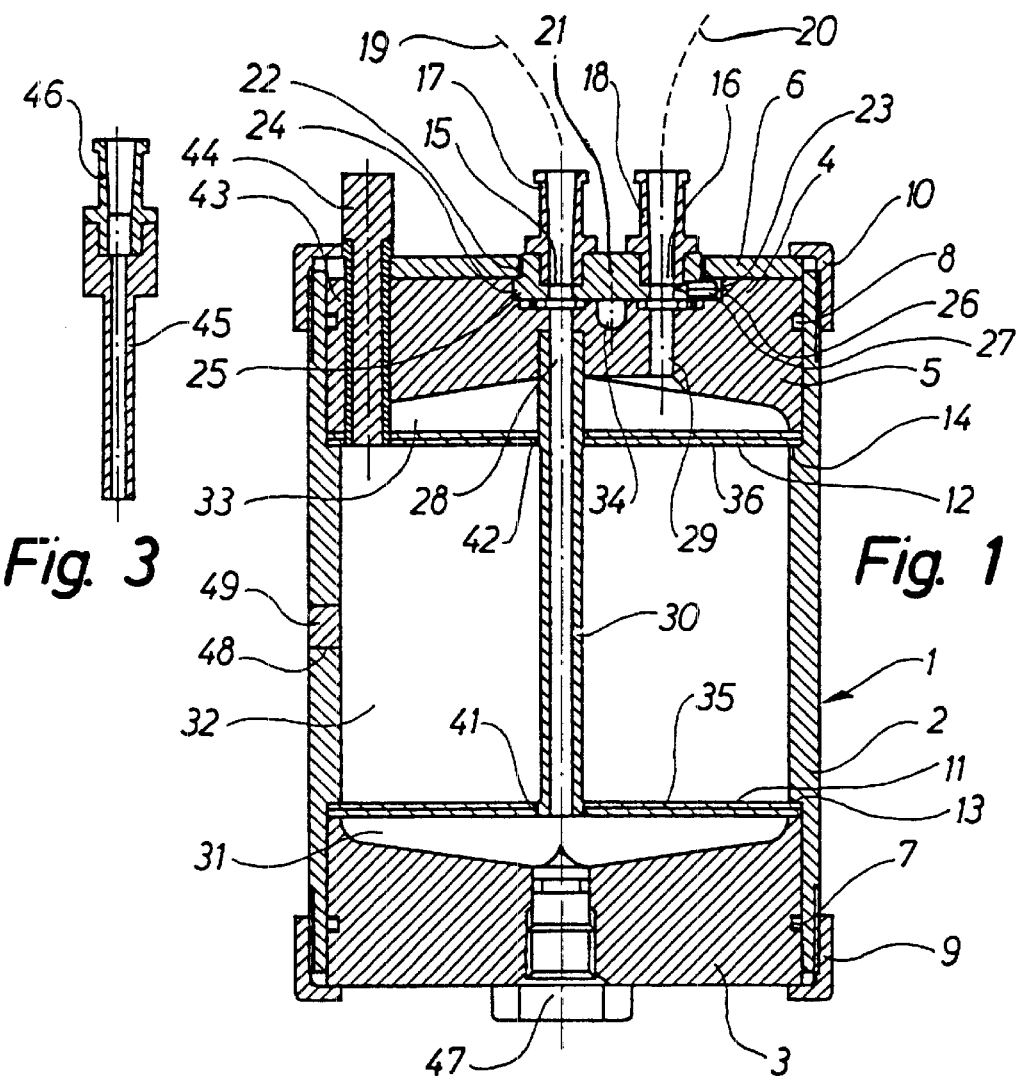
FIG. 1 is an axial sectional view through the apparatus according to the invention.
FIG. 3 illustrates an insertion means to be used by the sterilising and filling of the apparatus with an adsorbent.
Figure 2:
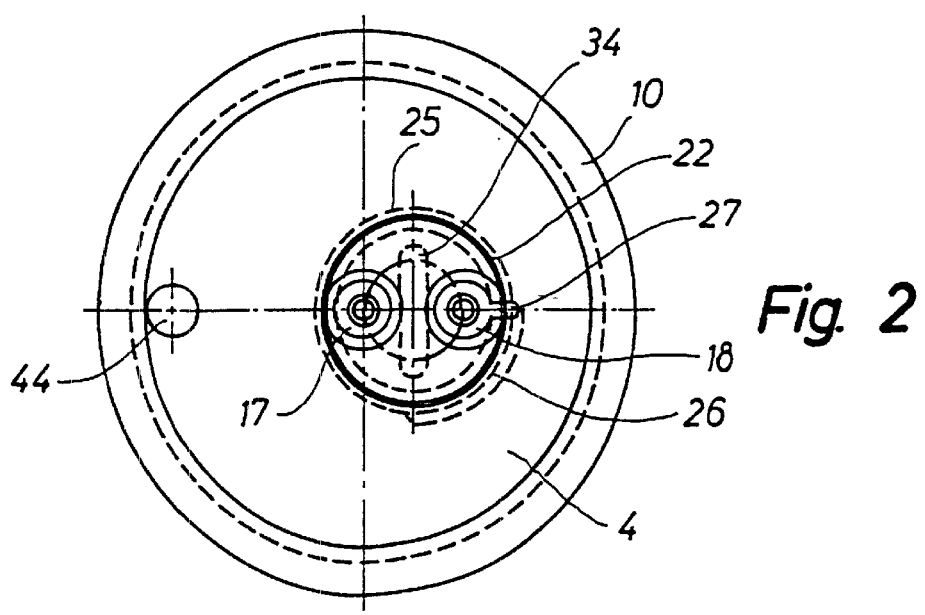
FIG. 2 is a top view of the same apparatus.

The apparatus illustrated in FIGS. 1 and 2 comprises a container designated the general reference numeral 1. This container comprises a tubular member 2 of a circular cross section and a bottom member 3 as well as a cover 4. The cover 4 comprises an inner cover member 5 and an outer cover member 6. These members are sealingly and permanently interconnected by means of suitable sealing rings 7 and 8, respectively, as well as screw caps 9 and 10, respectively, a filter unit 11 and 12 described in greater detail below being tightened between the bottom member 3 and the inner cover member 4 as well as corresponding circumferential abutment faces 13 and 14, respectively. These abutment faces are provided on the inner side of each end of the tubular member 2 of the container 1.

An inlet 15 and an outlet 16 are provided in the cover of the container 1. The inlet 15 and the outlet 16 comprise their respective stubs 17 and 18 for connection of an inlet conduit 19 and an outlet conduit 20, respectively. Here these conduits are only indicated by means of dotted lines, and they form part of a conduit system not shown in greater detail for extracorporeal circulation of blood from a patient. Each stub 17 and 18 is shaped such that they can be connected to the associated conduit by means of a Luer-coupling known per se.

The inlet stub 17 and the outlet stub 18 are secured in a disc-shaped valve means 21 arranged in a circular opening 22 in the outer cover member 6 and a recess 23 provided in the inner cover member 5 inside said outer cover member 6. The disc-shaped valve means 21 comprises a radially projecting circumferential flange 24 which engages a corresponding recess 25 along the periphery of the recess 23 in the inner cover member 5, whereby said valve means 21 with the stubs 17 and 18 is retained in the cover 4 in such a manner that it can rotate when the stubs 17 and 18 are manually activated. A groove 26 is provided in connection with the above recess 25, said groove extending 90° around along said recess. A pin 27 engages the groove 26, said pin 27 being secured in the valve means. The said groove 26 and the pin 27 co-acting therewith allow the valve means to be turned 90° forwards and backwards between two functional positions. The drawing indicates one functional position in which the inlet stub 17 and the outlet stub 18 directly oppose their respective passages 28 and 29, said passages extending directly through the inner cover member 5. A rigid transfer tube 30 is secured coaxially to the passage 28 opposite the inlet stub 17. This transfer tube extends from the inner cover member 5 and coaxially through the container and subsequently centrally through the filter units 11 and 12 to an opening at the chamber, viz. the inlet chamber 31, being defined between the bottom member 3 of the container 1 and the adjacent filter unit 11. A second chamber 32 is defined between the two filter units 11 and 12, said second chamber being adapted to receive an adsorbent of a conventionally known type, such as an avidine agarose mixture. A third chamber, viz. an outlet chamber 33, is defined between the inner cover member 5 and the adjacent filter unit 12, said third chamber communicating directly with the outlet stub 18 through the passage 29 in the position shown of the valve means 21. The sealing connection between the valve means 21 and the inner cover member 5 is as shown ensured by means of suitable sealing rings.

A turning of the valve means 21 into its second functional position, viz. 90° clockwise compared to FIG. 2, has the result that the inlet stub 17 and the outlet stub 18 enter a connection with their respective ends of a short channel 34 shaped in the adjacent side of the inner cover member 5.

Figure 4:
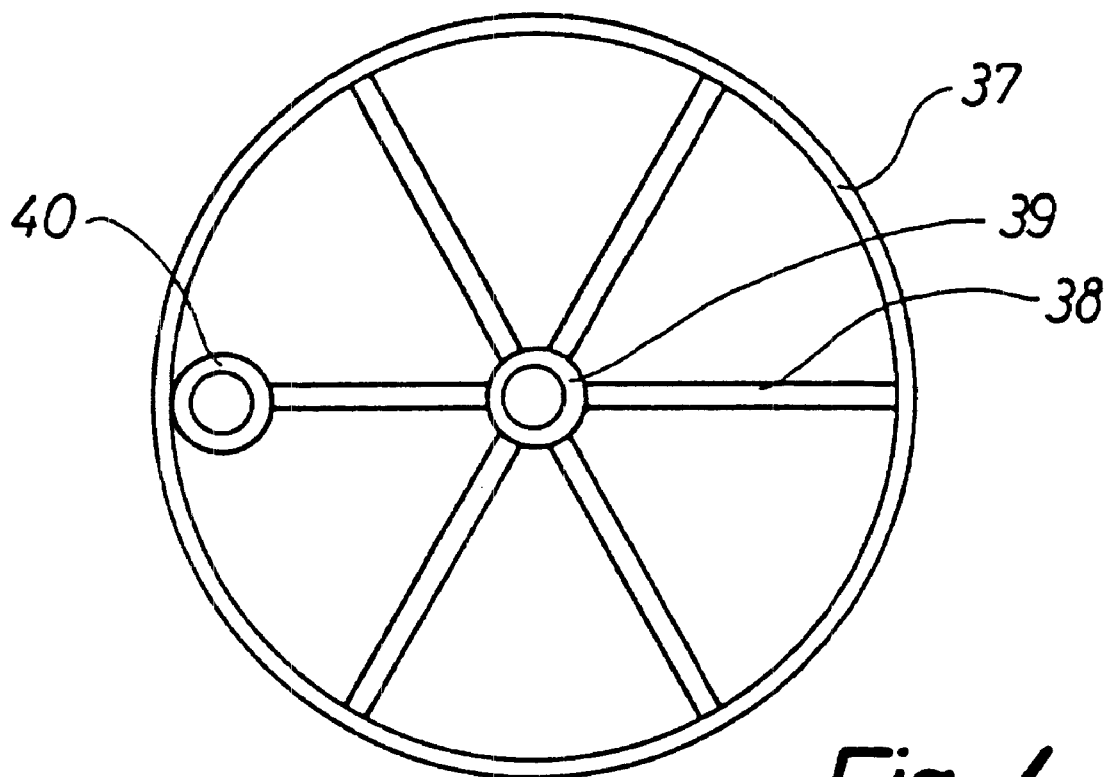
FIG. 4 illustrates an embodiment of a filter unit to be used in the apparatus according to the invention.

When the stubs 17 and 18 are manually operated, the valve means 21 can thus be moved forwards and backwards between the two functional positions according to desire. The two filter units comprise a circularly cut filter cloth in form of a perforated plastic sheet, one embodiment of said filter units appearing from FIG. 4. The perforated plastic sheet allows preferably passage of particles smaller than or equal to 70 $\mu$m. This filter cloth is indicated in FIG. 1 at the reference numerals 35 and 36. In order to ensure the stability of the filter units 11 and 12, the filter cloth 35 and 36 is embedded in a plastic structure 37 resembling a wheel with spokes 38 and a central ring 39. In addition, an additional ring 40 is provided, cf. the more detailed description below. The plastic structure 37 is integrally shaped, and the filter cloth 35, 36 is removed inside the ring 39 after the moulding. The central ring 39 in the filter units 11 and 12 are dimensioned in such a manner that it co-operates with a corresponding, circumferential groove 41 and 42 on the outer side of the transfer tube 30 by way of a snapping effect. The transfer tube 30 is of a slightly smaller diameter in the area between the above grooves.

As illustrated in FIG. 2, a through liner tube 43 is mounted adjacent the periphery of the cover 4, the inner end of said liner tube sealingly engaging the said second ring 40 in the filter unit 12 adjacent the cover 4. In the state of the apparatus shown in FIG. 1, a plug 44 is provided inside the liner tube 43. During the ready-making of the apparatus this plug is replaced by a passage unit 45 with an associated stub 46, cf. FIG. 3.

The two filter units 11 and 12 are identically shaped. When a filter unit is to be used as the filter unit 12, i.e. engaging the liner tube 43 as mentioned above, the filter cloth 36 is also removed inside the ring 40.

For the ready-making of the apparatus, a sealingly closable plug 47 is also provided in the bottom member 3.

Likewise, an opening 48 is provided in the tubular member 2 of the container 1, said opening 48 being used at the filling of adsorbent into the chamber 32. This opening 48 is closed after the filling procedure by means of a plug 49.

The use of the apparatus illustrated in FIGS. 1 and 2 implies that an initial sterilising of said apparatus is performed in a conventionally known manner followed by a filling of the chamber 32 with a suitable adsorbent under sterile conditions. Subsequently, the apparatus is coupled to the inlet conduit 19 and outlet conduit 20 of the blood circulation system. While the valve means is placed in the functional position shown in FIGS. 1 and 2, the blood enters through the inlet stub 17 and flows through the transfer tube 30 so as to flow out in the inlet chamber 31. Then the blood continues through the filter unit 11 and through the adsorbent in the adsorption chamber 32. Thereafter the blood flows through the filter unit 12 into the outlet chamber 33 and subsequently out of said chamber through the outlet stub 16 and back to the patient in a purified state.

In use of the apparatus the valve means 21 is rotated according to desire into the second functional position in which the blood can flow through the bypass-forming channel 34 directly from the inlet 15 to the outlet 16 in various situations, cf. the introduction to the description.

The described apparatus is manufactured of relatively simple members by way of injection moulding. The manufacture employs preferably environmentally neutral plastic materials, such as polycarbonate. The individual members are assembled by means of relatively simple means, and the apparatus is easy to operate. After use, the apparatus is discarded in a conventionally known manner.

The invention has been described with reference to a preferred embodiment. Many modifications can be carried out without thereby deviating from the scope of the invention. The valve means may for instance be adapted to a rectilinear displacement forwards and backwards between its functional positions. In addition, some of the members, such as the inlet stub 17 and the outlet stub 18 as well as the valve means 21, may be integrally shaped. The filter units may also be manufactured in various ways.

As mentioned the invention is particularly suited for use in connection with removal of exogenous elements from blood or blood plasma. The invention can, of course, also be used for removing endogenous elements, such as autoantibodies, antidonor antibodies, xenoantibodies and LDL (ow Density Lipoprotein), by a suitable choice of adsorbent.

What is claimed is:

1. An apparatus for removing elements from blood or plasma flowing in an extracorporeal blood circulation system of a patient, said apparatus comprising a container comprising, in sequence, an inlet chamber, an adsorption chamber for receiving an adsorbent, and an outlet chamber, said container also comprising a plurality of filter units for filtering the blood or plasma, including a first filter unit between the outlet chamber and the adsorption chamber and a second filter unit between the adsorption chamber and the inlet chamber, and a container wall portion that, with the first filter unit, defines the outlet chamber, said container wall portion comprising (a) an inlet and an outlet adjacent one another, (b) a plurality of passages, including a first passage that communicates with a transfer channel that extends from the first passage to the inlet chamber, and a second passage that communicates with the outlet chamber, (c) a bypass channel having first and second ends, and (d) valve means for connecting the inlet and the outlet with the respective first and second passages in a first arrangement of the valve means and for connecting the inlet and the outlet with the respective first and second ends of the bypass channel in a second arrangement of the valve means, said apparatus further comprising means for controlling movement of the valve means between said first and second arrangements.

2. An apparatus as claimed in claim 1, wherein the means for controlling movement comprises an inlet stub and an outlet stub connected to the valve means.

3. An apparatus as claimed in claim 2, wherein the valve means is rotatable.

4. An apparatus as claimed in claim 3, wherein the container wall portion comprises a cover including an inner cover member and an outer cover member, said outer cover member comprising an opening surrounding said valve means, said valve means comprising an at least partially circumferential, radially projecting flange which is received in a recess between the inner and outer cover members, and stopping means for stopping rotation of the valve means with the valve means in either of the first or second arrangements.

5. An apparatus as claimed in claim 4 wherein the container has an axial symmetry, the first passage and the transfer channel being disposed coaxially to an axis of symmetry of the container.

6. An apparatus as claimed in claim 5, wherein each of the plurality of filter units is disc-shaped and comprises a porous filter cloth embedded in a carrying plastic structure.

7. An apparatus as claimed in claim 6, wherein each filter unit is retained in sealing abutment with a circumferential abutment face on an inner wall of the container, the second filter unit being retained by a separately secured bottom member, said first filter unit being retained by the inner cover member.

8. An apparatus as claimed in claim 7, wherein the transfer channel is formed by a tube that is connected to the inner cover member, said tube comprising outer circumferential grooves that snap with a central annular member of the carrying structure of each filter unit.

9. An apparatus as claimed in claim 1, comprising the adsorbent in the adsorption chamber.

* * * * *